United States Patent
Steidle et al.

(10) Patent No.: US 12,159,441 B2
(45) Date of Patent: Dec. 3, 2024

(54) SURGICAL MICROSCOPE HAVING A CONNECTION REGION FOR ATTACHING A PROTECTIVE GLASS MODULE

(71) Applicant: Carl Zeiss Meditec AG, Jena (DE)

(72) Inventors: Manuel Steidle, Aalen (DE); Andreas Raab, Neuler (DE)

(73) Assignee: Carl Zeiss Meditec AG, Jena (DE)

( * ) Notice: Subject to any disclaimer, the term of this patent is extended or adjusted under 35 U.S.C. 154(b) by 140 days.

(21) Appl. No.: 17/947,119

(22) Filed: Sep. 17, 2022

(65) Prior Publication Data
US 2023/0093637 A1   Mar. 23, 2023

(30) Foreign Application Priority Data
Sep. 17, 2021   (DE) .................. 10 2021 210 318.9

(51) Int. Cl.
*G06V 10/22*   (2022.01)
*A61B 46/10*   (2016.01)
(Continued)

(52) U.S. Cl.
CPC ........... *G06V 10/225* (2022.01); *H04N 9/797* (2013.01); *H04N 23/55* (2023.01); *H04N 23/56* (2023.01); *A61B 46/10* (2016.02)

(58) Field of Classification Search
CPC ...... G06V 10/225; H04N 9/797; H04N 23/55; H04N 23/56; A61B 46/10;
(Continued)

(56) References Cited

U.S. PATENT DOCUMENTS 5,502,598 A * 3/1996 Kimura ............. A61B 1/00183
359/830
7,889,423 B2 * 2/2011 Reimer .................. A61B 90/36
359/368
(Continued)

FOREIGN PATENT DOCUMENTS

DE   102015225009 A1   6/2017
DE   102017109698 A1   11/2018
(Continued)

OTHER PUBLICATIONS

Office Action issued in German Patent Application No. DE 10 2021 210 318.9, dated Jan. 20, 2022 (from which this application claims priority) and English language translation thereof.

*Primary Examiner* — Jared Walker
(74) *Attorney, Agent, or Firm* — Ewers IP Law PLLC; Falk Ewers

(57) ABSTRACT

A surgical microscope includes an image capture unit having an image sensor, a detection beam path, an image evaluation unit, a connection region for attaching a protective glass module with an objective protective glass. The image sensor has a detection region which has a used detection region for capturing the object region, and a partial detection region, which is not assigned to the used detection region. The image capture unit is configured such that, when the protective glass module with the objective protective glass is arranged at the connection region, a detail of the protective glass module with the objective protective glass is capturable by the partial detection region of the image sensor. The image evaluation unit is configured to generate a signal when an objective protective glass is detectable by the evaluation of the image data of the partial detection region of the image sensor.

16 Claims, 7 Drawing Sheets

(51) Int. Cl.
  *H04N 9/797*  (2006.01)
  *H04N 23/55*  (2023.01)
  *H04N 23/56*  (2023.01)

(58) Field of Classification Search
  CPC ............ A61B 2034/2065; A61B 90/30; A61B 2090/371; A61B 90/05; A61B 90/20; G02B 27/0006; G02B 21/0012; G02B 27/0988
  See application file for complete search history.

(56) References Cited

U.S. PATENT DOCUMENTS

| | | | |
|---|---|---|---|
| 9,948,842 B2* | 4/2018 | Johnson | G06T 7/001 |
| 10,156,718 B2 | 12/2018 | Koenig et al. | |
| 10,330,927 B2* | 6/2019 | Hoegele | G02B 21/361 |
| 10,989,908 B2 | 4/2021 | Amthor et al. | |
| 11,226,477 B2* | 1/2022 | Regensburger | H04N 23/69 |
| 11,506,875 B2* | 11/2022 | Mueller | G02B 25/001 |
| 2006/0203330 A1* | 9/2006 | Moeller | G02B 21/0012 359/377 |
| 2014/0313312 A1 | 10/2014 | Gaiduk et al. | |
| 2019/0278074 A1* | 9/2019 | Gögler | G02B 21/086 |
| 2019/0328464 A1* | 10/2019 | Saur | G02B 21/0012 |
| 2019/0369031 A1* | 12/2019 | Niikura | G05B 23/0283 |
| 2020/0057291 A1 | 2/2020 | Haase et al. | |

FOREIGN PATENT DOCUMENTS

| | | |
|---|---|---|
| DE | 102019114117 B3 | 8/2020 |
| EP | 2793069 A1 | 10/2014 |
| JP | H1090609 A | 4/1998 |
| WO | 2011090633 A2 | 7/2011 |

* cited by examiner

SURGICAL MICROSCOPE HAVING A CONNECTION REGION FOR ATTACHING A PROTECTIVE GLASS MODULE

CROSS REFERENCE TO RELATED APPLICATIONS

This application claims priority to German patent application DE 10 2021 210 318.9, filed Sep. 17, 2021, the entire content of which is incorporated herein by reference.

TECHNICAL FIELD

The disclosure relates to a surgical microscope having an image capture unit with an image sensor and a connection region for attaching a protective glass module.

BACKGROUND

Modern surgical microscopes include at least one image capture unit with an image sensor, for example a camera, for recording images or capturing additional data of a region to be operated, also referred to as surgical site.

During surgery, surgical microscopes are at risk of contamination caused by the region to be operated. A surgical microscope is therefore covered in surgical situations with a sterile cover sheet, which is also referred to as drape. The region in front of the observation optical unit of the surgical microscope is separately protected against contamination by a protective glass module. The protective glass module is mechanically attached to the surgical microscope at a connection region and includes a transparent objective protective glass. The drape is mounted on the outer periphery of the protective glass module and, together with the protective glass module, forms a hygienically closed protective barrier around the surgical microscope.

Inserting an objective protective glass into the beam path of the surgical microscope can cause the image that is to be observed or is recorded by the image sensor to be optically influenced, for example in the form of an image offset or a distortion. This can be important when the images recorded by the image capture unit are computationally processed. In particular, the two-dimensional or spatial assignment of position information can be changed and falsified in this way.

SUMMARY

It is therefore an object of the disclosure to provide an apparatus for a surgical microscope, with which apparatus it is possible to reliably detect the insertion of an objective protective glass into the beam path of a surgical microscope.

The object is achieved by a surgical microscope as described herein.

According to an aspect of the disclosure, a surgical microscope includes an image capture unit with an image sensor. A detection beam path is guided from an object region to the image sensor of the image capture unit. The surgical microscope includes an image evaluation unit, which is connected to the image sensor.

The surgical microscope includes a connection region for attaching a protective glass module with an objective protective glass, which connection region is configured such that, in an appropriate protective glass module which is attached to the connection region, the objective protective glass has been inserted into the detection beam path.

The image sensor has a detection region, wherein the detection region has a used detection region for capturing the object region. The detection region has a partial detection region, which is not assigned to the used detection region.

The image capture unit is configured such that, when the protective glass module with the objective protective glass is arranged at the connection region, a detail of the protective glass module with the objective protective glass is capturable by the partial detection region of the image sensor. The image evaluation unit is configured to produce a signal when an objective protective glass is detectable by the evaluation of the image data of the partial region of the image sensor.

The surgical microscope makes it possible for a user, for example a surgeon, to view in magnified fashion an object region with an object plane, at a surgical site. The object plane defines a central plane. Above and below the central plane, a region defined by the depth of field can be imaged sharply by the surgical microscope. The surgical microscope includes an image capture unit with an image sensor. A detection beam path is guided from the object region to the image sensor such that the object region is imaged on the image sensor. The detection beam path can be guided through an objective. A plurality of optical components, for example further objectives, zoom systems or beam splitters, can also be arranged in the detection beam path.

The image sensor captures an individual image or a plurality of individual images, for example a video sequence, of the object region. The evaluation and data-technological processing of the images captured by the image sensor are performed in the image evaluation unit, which is connected to the image sensor. The image evaluation unit is a data processing unit.

The surgical microscope includes a connection region for attaching a protective glass module with an objective protective glass. The protective glass module protects the optical unit of the surgical microscope that is directed toward the object region against contaminations caused by the surgical site. The protective glass module can be mechanically connected to the surgical microscope with a form fit via the connection region thereof. The fixed connection of the protective glass module to the connection region is easily releasable. The mounting or removal of the protective glass module with the objective protective glass on or from the surgical microscope is quickly and easily possible by way of the connection region.

The position and alignment of the protective glass module with the objective protective glass in relation to the surgical microscope are distinctly defined by way of the connection region. If the protective glass module is attached to the connection region with a form fit, the objective protective glass is thus arranged in the detection beam path with a distinct alignment and at a defined distance relative to the optical unit of the surgical microscope.

The image sensor of the image capture unit has a detection region. The detection region has a used detection region, which is assigned to the capturing of the object region. The detection beam path is guided from the object region to the used detection region of the image sensor. In dependence on an optical unit arranged in the detection beam path and the size of the image sensor, a defined detail of the object region is imaged onto the used detection region of the image sensor. The image data of the used detection region can be used for visualizing the object region, the surgical site, on a display apparatus. The image data of the used detection region can also be used for a surgical microscope functionality, for example a tracking function.

The detection region of the image sensor has a partial detection region, which is not assigned to the used detection region.

When a protective glass module with the objective protective glass is attached to the connection region, the objective protective glass is situated in the detection beam path at a defined position and with a defined alignment relative to the connection region of the surgical microscope. The objective protective glass forms part of the protective glass module. A detail of the protective glass module with the objective protective glass is then capturable by the partial detection region of the image sensor. In this way, a partial detection region of the image sensor, which region is not used for viewing the object region in the used detection region, is used for detecting the objective protective glass in the detection beam path.

The image data of the partial detection region of the image sensor are processed in the image evaluation unit. Since a separate sensor region, the partial detection region, is used on the image sensor for detecting a protective glass module with an objective protective glass, data can be processed very quickly. When the data processing in the image evaluation unit calculates after the analysis of the image sensor data of the partial detection region the result that a protective glass module with an objective protective glass has been inserted into the detection beam path, a signal is output.

This advantageously makes it possible to reliably detect a protective glass module with an objective protective glass in the detection beam path.

The surgical microscope includes a system which makes it possible with the image capture system integrated in the surgical microscope to detect whether the surgical microscope is used with or without the objective protective glass. It is no longer necessary to install additional sensors for detecting an objective protective glass at the surgical microscope. Additional sensors would take up installation space and require cabling.

When an objective protective glass is detected in the detection beam path by way of the evaluation of the image data of the partial region of the image sensor, a signal is output.

The signal output by the image evaluation unit can advantageously be processed in further functional units of the surgical microscope and control a subsequent data processing.

The signal can be used for controlling further processing steps in the image evaluation unit. The processing of the signal in additional data processing units of the surgical microscope is also possible.

In one exemplary embodiment, the signal can be used in order to computationally correct the captured image data of the used detection region. Optical image errors caused by the objective protective glass can be removed by calculation. Image errors, such as an image offset, that is to say a lateral image displacement, or a distortion, can be computationally corrected. The correction of the image data can then be effected either in the image evaluation unit itself or in a different computation unit in which image data are processed.

If position information is determined from the image data, that information is thus computationally correctable. The two-dimensional or spatial assignment of position information can be corrected in this way. Correct position information is of great importance in tracking functionalities. This is why the correction of even small image errors can be necessary too.

The signal can also be used to output information via an operator interface, for example via a graphical user interface, which is also referred to as GUI.

In one exemplary embodiment, the signal can also be used for correcting an autofocus function of the surgical microscope.

It is also possible to detect an objective protective glass if the protective glass module is constructed in two parts. In a two-piece construction, the objective protective glass is detachably connected to the protective glass module. The part of the protective glass module that remains attached to the connection region of the surgical microscope when the objective protective glass is swapped is referred to as protective glass adapter. During the interchange of the objective protective glass, the protective glass adapter, to which a drape can also be attached, remains in place at the connection region of the surgical microscope. It is possible in this way to easily swap out a contaminated objective protective glass, for example during surgery, without the entire protective glass module being interchanged.

In this case, the detection of the objective protective glass is also reliably possible. This is because the signal is produced only when an objective protective glass is detectable by the evaluation of the image data of the partial region of the image sensor.

A surgical microscope can also be operated with a sterile protective sleeve without a protective glass module or with a two-piece protective glass module without objective protective glass. For example, the objective protective glass could have been removed after a contamination and the mounting of a new objective protective glass could have been forgotten or omitted. The reliable detection of an objective protective glass in the detection beam path is ensured by the disclosure even in those cases.

In one exemplary embodiment, the surgical microscope can be a conventional optical stereo surgical microscope with a main objective, in which the object region, the surgical site, can be viewed through eyepieces. A beam splitter is arranged in the observation beam path, with the result that the object region is also imaged at least partially onto the image sensor of an image capture unit. In a stereo surgical microscope, the image capture unit can also include two image sensors. The optical axes of the observation beam path and of the detection beam path are in this exemplary embodiment formed coaxially between the object region and the beam splitter. The observation beam path is guided from the beam splitter further to the eyepieces. The detection beam path is guided from the beam splitter further to the image sensor.

In an alternative exemplary embodiment, the surgical microscope can also be configured as a purely digital surgical microscope, in which the object region is recorded exclusively with the image capture unit and is presented on a display apparatus, for example a monitor. The detection beam path is guided from the object region to the image capture unit. In stereoscopic surgical microscopes, the image capture unit is of stereoscopic design and includes at least two image sensors. If there is only one image sensor, an observation beam path is identical to the detection beam path. If there are a plurality of image sensors, at least one beam path which is guided from the object region to an image sensor is a detection beam path.

In an alternative exemplary embodiment, the surgical microscope can also be configured as a hybrid system with a main objective. The hybrid system can both enable observation through eyepieces and also have one or more image capture units for recording the object region. The image capture unit can also be arranged such that the optical axes of an observation beam path guided to the eyepieces and of a detection beam path guided to an image capture unit do not extend coaxially between the object region and the main objective but form a small angle.

The image recorded by the image capture unit and presented by a display apparatus can be displayed as a two-dimensional or three-dimensional image.

In an alternative exemplary embodiment, a surgical microscope can also have image capture units that are assigned merely to the observation of the object region and further image capture units that are assigned to additional functions. One of these additional functions can be formed by a tracking function integrated in the surgical microscope for tracking surgical instruments. The image sensor of the image capture unit which is assigned to a tracking function has a used detection region that is used for capturing the object region for the tracking functionality. A partial detection region of the image sensor which is not assigned to the used detection region can be used for detecting an objective protective glass in the detection beam path.

The image capture unit has an image sensor and can furthermore include an optics unit. The image capture unit with the image sensor can be a camera, for example.

The imaging of the object region on the image sensor does not have to be complete, but can also be limited to a smaller detail, for example the core region of the operating region. The object region can be imaged roundly through the optical unit of the surgical microscope, and a detail thereof can be imaged on the image sensor on a square or rectangular sensor region. In one exemplary embodiment, the object region that is capturable by the image sensor can also be larger than the observation region which is presentable for example on a display apparatus. In this way, surgical instruments that project into the peripheral region of the object region are also capturable.

The image evaluation unit is a data processing unit that can process the image data of an image sensor. The image evaluation unit can be a computer. In one exemplary embodiment, the image evaluation unit can also be formed by a signal processor, a microcontroller, or a graphical card unit.

A protective glass module can be embodied in one piece, two pieces or more pieces.

In the single-piece embodiment of a protective glass module, the protective glass adapter and the objective protective glass are produced inseparably from one piece or are fixedly connected to one another. An objective protective glass can be attached to the surgical microscope only together with the entire protective glass module. It is not possible to separate the objective protective glass from the protective glass module.

In a two-piece embodiment, the protective glass module includes a protective glass adapter and an objective protective glass. The protective glass adapter includes, on the first side, a connection part that is compatible with the connection region of the surgical microscope, with the result that the protective glass adapter can be mechanically attached with a form fit to the surgical microscope. The protective glass adapter can be embodied as a ring, for example. On the opposite, second side, the protective glass adapter includes a receptacle for the objective protective glass. The protective glass adapter can include for example a guide so that the objective protective glass can be inserted into this guide. The protective glass adapter can additionally be connected to a drape to form a sterile barrier around the surgical microscope. The two-piece embodiment of a protective glass module has the advantage that the objective protective glass can simply be interchanged during surgery, without the protective glass adapter or the drape having to be changed or touched. The protective glass adapter, the objective protective glass, and the drape are generally single-use products.

In the two-piece embodiment of the protective glass module, the insertion or removal of the objective protective glass into or from the detection beam path can be detected even if the protective glass adapter remains permanently at the connection region of the surgical microscope during surgery.

The optically relevant region of the objective protective glass can be formed by a plane-parallel thin plate. The objective protective glass is positioned at a defined inclination, in one exemplary embodiment at an angle of 15° to a plane that is orthogonal to the detection beam path, and at a defined distance relative to the optical unit of the surgical microscope that is to be protected. The defined inclination of the objective protective glass prevents disturbing back-reflections when observing the object region from occurring. This allows the user, for example a surgeon, a reflection-free view of the surgical site and thus to work in a relaxed manner, without any disturbing influence by the objective protective glass.

The attachment of the protective glass module to the connection region of the surgical microscope can take place, for example, by a thread, by clamping, or by magnetic force. A defined distance can be achieved for example by connecting two plane surfaces, wherein a first plane surface is formed on the surgical microscope and a second plane surface is formed on the protective glass module. The attachment surface can also be formed as a guide or a cone. A mechanical abutment, a latching point or a marking can ensure that the protective glass module is attached at a distinct position on the surgical microscope.

The attachment force is matched to the weight of the protective glass module with the objective protective glass and a drape attached thereto in order to prevent the protective glass module from being able to drop into the surgical region. Owing to the connection region at the surgical microscope, the protective glass module with the objective protective glass can be swapped very quickly and easily. Before every surgery where there is a risk of contamination of the microscope optical unit, a new protective glass module is attached to the surgical microscope at the connection region.

The term protective glass module, protective glass adapter or objective protective glass does not indicate a material designation. An objective protective glass does not need to be made from the material glass. An objective protective glass is typically produced from a transparent plastic. The material plastic has the advantage that it is more lightweight than glass. The safety for the surgical site in the case of a breakage would be larger using the material plastic than in the case of glass.

An interchangeable objective protective glass is sold, for example, under the name "Vision Guard."

The signal is an output form for the result of the image evaluation unit of whether there is an objective protective glass in the detection beam path. A signal can form a data signal at an output of the image evaluation unit. The signal can be generated by a voltage signal, for example by a positive voltage at an output. Alternatively, the signal can be present at an "open collector" output or be made available galvanically isolated via a relay output or optocoupler output. Alternatively, the signal can be output to an output by a pulse signal or as a data signal via a data bus. A signal can be generated by setting or resetting a bit or byte in a memory. A signal can also be defined by a variable in a software. By setting or resetting the variables to a defined value, a signal can be output.

The signal can consequently control subsequent data processing for the image data of the image sensor. The signal can also be evaluated so as to be unnoticeable by the user, and so correction of the image data takes place automatically when the signal for the detection of an objective protective glass in the detection beam path is output. However, in an alternative exemplary embodiment, this signal can also be output, possibly additionally, on a screen. Outputting the signal as a visual or acoustic signal is also conceivable.

In one exemplary embodiment, a signal can be output to a user when an objective protective glass has been removed but no new objective protective glass has been mounted again.

In one exemplary embodiment of the disclosure, the surgical microscope includes an illumination apparatus for illuminating the object region with illumination light, wherein illumination light reflected at the objective protective glass in the partial detection region of the image sensor is detectable if the protective glass module with the objective protective glass is arranged at the connection region.

The surgical microscope can be equipped with an illumination apparatus for illuminating the object region, that is to say the surgical site. The illumination apparatus can include an illumination optical unit. The illumination light is guided along an illumination beam path or at least one illumination path to the object region. If a protective glass module with an objective protective glass is mounted on the connection region and the objective protective glass is located in the detection beam path, some of the illumination light is reflected at the objective protective glass. This reflection of the illumination light at the objective protective glass is referred to as back-reflection. At least some of the back-reflected illumination light is then incident on the partial detection region of the image sensor. This detected illumination light is evaluable by the image evaluation unit, with the result that the image evaluation unit can output the signal that an objective protective glass is arranged in the detection beam path. The illumination light is not limited to the wavelength range which is visible to the human eye of approximately 380 nm to 780 nm. The illumination light can also include spectral components that lie below or above that range. In one exemplary embodiment, the illumination light can emit infrared light with a wavelength of larger than 780 nm.

When the objective protective glass is not arranged in the detection beam path, the illumination light is not reflected at the objective protective glass either. Consequently, no reflected illumination light is incident on the partial detection region of the image sensor either. The evaluation of the image data for the partial detection region in the image evaluation unit leads to the result that no objective protective glass is located in the detection beam path. The signal that an objective protective glass is located in the detection beam path is consequently not output by the image evaluation unit.

By evaluating the back-reflection of illumination light, it is thus detectable whether or not an objective protective glass has been inserted into the detection beam path.

The objective protective glass is positioned with a defined inclination and at a defined distance with respect to the detection beam path and the illumination apparatus, which can include an illumination optical unit. It is thus possible to ensure that the direct back-reflection from the objective protective glass is permitted only on a peripheral region of the image sensor on which the partial detection region is defined. The positioning of the illumination apparatus, of the detection beam path and of the objective protective glass are matched to one another in a manner such that the used detection region on the image sensor is not at all affected by the back-reflection, or is affected only to a very minor degree. This ensures that the used detection region, that is to say the detection region of the image sensor, which is defined for capturing the object region, is not adversely affected by back-reflected light. The observation of the object region or a surgical microscope functionality derived from the observation of the object region, for example a tracking function, is not disturbed by reflected illumination light.

This is possible because the used detection region does not take up the entire detection region of the image sensor. The used detection region is defined for example in a partial region or a central region of the image sensor. The partial detection region is defined in a peripheral region of the image sensor. If a back-reflection of illumination light is detected in the specified partial detection region of the image sensor, an objective protective glass is present in the detection beam path; otherwise it is not.

In one exemplary embodiment, the relative positioning of the components illumination apparatus, detection beam path, and protective glass module with objective protective glass at the surgical microscope according to an aspect of the disclosure can deviate from a typical positioning of these components in a standard surgical microscope so as to achieve the back-reflection onto the partial detection region. The typical positioning in a standard surgical microscope can be configured such that no disturbing back-reflections occur on the entire sensor surface of the image sensor of the surgical microscope. An optically free passage of the objective protective glass can include in each case one or more illumination apparatuses and one or more image capture units.

In one exemplary embodiment, the surface of the objective protective glass is configured to be particularly reflective at one location, for example by way of a reflective treatment. The illumination light emitted by the illumination apparatus can be reflected at this point of the objective protective glass with a relatively high intensity and detected by the partial detection region of the image sensor. The reflection of illumination light is thus larger and the detectable sensor value in the partial detection region is higher than in the case of a purely transparent objective protective glass.

In one exemplary embodiment of the disclosure, the image evaluation unit is configured such that the image data of the partial detection region are evaluable for a diffractive optical element on or in the objective protective glass.

A diffractive optical element can be arranged on or in the objective protective glass. The diffractive optical element makes targeted beam steering of illumination light, or the targeted influencing of the direction of the reflection path, possible. Since the emission angle of the reflected light is thus definable, this increases the number of positions at which the diffractive optical element can be arranged at the objective protective glass.

In one exemplary embodiment of the disclosure, the surgical microscope includes a stop, which is arranged in the detection beam path upstream of the image sensor, wherein the stop has a first opening that is assigned to the used detection region and has a second opening that is assigned to the partial detection region.

A stop that is arranged upstream of the image sensor delimits the field of view on the image sensor and has the effect of a field stop. A first clearance or first opening in the stop is assigned to the used detection region of the image sensor. A second clearance or second opening in the stop is assigned to the partial detection region of the image sensor.

The first opening of the stop is the same size as the used detection region and delimits the latter on the image sensor. The second opening of the stop defines the partial detection region with which the detail of the protective glass module with the objective protective glass is capturable by the image sensor. The partial detection region is sharply delineated by the stop from the surrounding individual sensors, which are also referred to as sensor pixels. For the above-described embodiment of the surgical microscope having an illumination apparatus, the second opening forms a defined opening for the back-reflected illumination light. In this way, the individual sensors to be evaluated on the image sensor are distinctly defined, resulting in a fast and simpler image evaluation. Only a relatively small number of individual sensors of the image sensor are required for the analysis of whether an objective protective glass is arranged in the detection beam path.

If a thin sensor protective plate is mounted upstream of the image sensor, the stop is arranged in the detection beam path upstream of the sensor protective plate. Due to the distance between the stop and the image sensor, the first opening and the second opening can also be embodied to be slightly larger than the fields of view on the image sensor assigned by the stop.

The stop advantageously reduces the radiation of reflection light that is incident on the image sensor. If a protective glass module is attached to the surgical microscope and the objective protective glass has been inserted into the detection beam path, the light reflected by the objective protective glass could have such a high radiant power that the used detection region is also negatively influenced thereby, at least in the peripheral region. The overexposure could manifest by way of the blooming effect on the used detection region and partial detection region. The blooming effect describes the formation of a bright spot around a local overexposure on an image sensor. The cause of this is that in specific sensor technologies, if the irradiation with photons is too great, the image sensors can reach the limit of the quantity of charge that can be stored and then possibly pass on charges to adjacent sensors. In this way, the blooming effect can have an effect on a number of image sensors.

The stop reduces the incoming radiant power of the back-reflected light on the image sensor and can prevent or significantly reduce a blooming effect on the used detection region and/or partial detection region. The stop reduces the incoming radiant power of the back-reflected illumination light on the partial detection region and/or used detection region of the image sensor to the required extent. In this way, the stop has also been advantageously inserted into the detection beam path to reduce the power of the back-reflected light onto the image sensor.

Advantageously, a relatively large stop, having at least the size of the image sensor, also simplifies the mounting and adjustment of the stop. Since this stop has two openings, only one individual stop element rather than two separate individual stops are required. Consequently, only one individual stop mount is also advantageously required, which makes simpler handing possible.

In an alternative exemplary embodiment of the disclosure, a stop is arranged in the detection beam path upstream of the image sensor, wherein the stop is smaller than the image sensor and the stop has only one individual opening, which is assigned to the partial detection region.

In this exemplary embodiment, a stop is arranged only upstream of the sensor section that is assigned to the partial detection region. The stop is smaller than the image sensor. The stop has an individual clearance, which is assigned to the partial detection region. Consequently, the stop covers only a delimited partial region of the image sensor. In this way, a very small stop can be used, which is delimited to the partial detection region. This exemplary embodiment can also be advantageous if the used detection region extends on the image sensor on two sides or three sides up to the periphery of the image sensor.

In one exemplary embodiment of the disclosure, the size of the partial detection region on the image sensor is smaller than the size of the used detection region on the image sensor.

A small partial detection region requires only a small number of individual sensors. Consequently, the majority of the individual sensors is available for the used detection region on the image sensor.

In one exemplary embodiment of the disclosure, the size of the partial detection region on the image sensor is between 0.1% and 10%, typically between 0.1% and 5%, with further preference between 0.1% and 3%, with particular preference between 0.1% and 1%, of the value of the size of the used detection region on the image sensor.

A small partial detection region includes a relatively small number of individual sensors. This increases the data processing speed. A small partial detection region allows larger utilization of the image sensor as the used detection region.

In one exemplary embodiment of the disclosure, the used detection region on the image sensor is rectangular.

An image sensor includes individual sensors, which are arranged in rows and columns. Consequently, the image sensor is typically rectangular. Owing to the rectangular shape of the used detection region, the surface area of the image sensor can be optimally used for the used detection region. In addition, display apparatuses, for example screens, are likewise rectangular, and as a result, the image data of the used detection region can be presented optimally on a display apparatus.

In one exemplary embodiment of the disclosure, the used detection region on the image sensor is round.

In viewing a surgical site through eyepieces of an optical surgical microscope, the object region is presented roundly. For this reason, it may be advantageous to define a round used detection region on the image sensor. The image data in the used detection region correspond to the object region that is observable through the eyepieces.

In one exemplary embodiment of the disclosure, the partial detection region is rectangular.

With a rectangular partial detection region, the sensor matrix of the column and row numbers to be evaluated is easily definable.

In one exemplary embodiment of the disclosure, the partial detection region is square.

With a square partial detection region, the sensor matrix of the row and column numbers to be evaluated is easily definable. The surface area of the partial detection region is maximal, based on the number of the rows and columns of the sensor matrix that are to be evaluated.

In one exemplary embodiment of the disclosure, the partial detection region is round.

With a round definition of the partial detection region, the ratio between the circumference and sensor surface area is particularly favorable. The number of the sensors to be evaluated is smaller than in the case of a rectangular sensor surface area. This results in fast data processing in the image evaluation unit.

In one exemplary embodiment of the disclosure, the partial detection region is separated from the used detection region by a sensor region that is assigned neither to the partial detection region nor to the used detection region.

Advantageously, the partial detection region is arranged so as to be separated from the used detection region. The partial detection region is defined at a distance from the used detection region. If a stop is arranged upstream of the image sensor, a stop can have a stop edge around the partial detection region. This enables particular protection for the used detection region against back-reflected illumination light.

In one exemplary embodiment of the disclosure, the image evaluation unit is configured such that the image data of the partial detection region are evaluable for an optical element in or on the objective protective glass.

An optical element that changes the optical property of the objective protective glass at the point that is detected by the partial detection region can be arranged in or on the objective protective glass. The optical element can therefore be designed to be small and can be arranged in a region of the objective protective glass that does not influence the assigned field of view of the used detection region. The optical element is captured only by the partial detection region and does not result in any adverse effect on the optical functionality of the surgical microscope.

An optical element is an element that changes an optical property or an optical attribute of the transparent objective protective glass in a manner such that good detectability on the part of the partial detection region is ensured. In one exemplary embodiment, the optical element can be formed by an optical structure, for example a grating or a diffractive optical element, with the result that an interference pattern or an intensity distribution is capturable by the partial detection region. In one exemplary embodiment, the optical element can bring about a change in the refractive index, for example by way of an optical coating. In one exemplary embodiment, an optical element can also be formed by a hologram. In one exemplary embodiment, the optical element can be formed by a lens structure. In one exemplary embodiment, the optical element can include a reflective treatment. In one exemplary embodiment, the optical element can be an image.

In one exemplary embodiment of the disclosure, the image evaluation unit is configured such that the image data of the partial detection region are evaluable for a stamp in the objective protective glass.

The objective protective gas is thus detectable by way of a stamp introduced into the objective protective glass. A stamp is a defined three-dimensional shape, which is either stamped into the objective protective glass in the form of a depression or has been applied as an elevation on the objective protective glass. In one exemplary embodiment, the stamp includes both elevated regions and depressed regions. The stamp can consist of the same material as the objective protective glass. The stamp can thus be transparent. Owing to the light changes of the different material thicknesses and edges in the stamping region, the objective protective glass is detectable in the partial detection region of the image sensor. A stamp can also already be introduced in the shaping tool, with which the objective protective glass is produced. The objective protective glass can be produced by way of injection molding or injection compression molding. Without any further working step, the stamp is consequently always located at exactly the same point in the objective protective glass. The image evaluation unit is configured to produce a signal when a stamp introduced into the objective protective glass is detectable by the evaluation of the image data of the partial detection region of the image sensor.

In one exemplary embodiment of the disclosure, image data of the partial detection region are evaluable for a stamp in the objective protective glass, wherein the stamp forms a geometric shape.

A geometric shape can be formed for example by a circle, an ellipse, a square, a rectangle, a rhombus, a triangle, a polygon, or a dot pattern. A geometric shape is easily detectable in the image evaluation unit by way of image analysis. Geometric shapes can have a simple or a complex form.

In one exemplary embodiment of the disclosure, the image evaluation unit is configured such that the image data of the partial detection region are evaluable for a logo on the objective protective glass.

A logo is a graphically designed symbol designated for identifying a company or a product. A logo may be two-dimensional or three-dimensional. The logo can be introduced into the objective protective glass or be applied on the objective protective glass as a quality feature. Checking for a logo can also ensure that an objective protective glass that has specific quality features has been used.

In one exemplary embodiment of the disclosure, the image evaluation unit is configured such that the image data of the partial detection region are evaluable for a stamp in the objective protective glass, with the stamp forming a logo.

The logo can be introduced into the objective protective glass in the form of a stamp. A stamp cannot be easily removed.

In one exemplary embodiment of the disclosure, the image evaluation unit is configured such that the image data of the partial detection region are evaluable for a pattern on the objective protective glass.

A pattern is a structure, which is characterized by a repeated, uniform and/or parallel presentation of lines, shapes or geometric elements. The structure can have a circular or linear arrangement. A pattern can therefore be advantageously applied over a large area of the objective protective glass. Owing to the repeated presentation of the structure, the pattern in the image data of the partial detection region can be more easily detected in the image evaluation unit even if a partial detection region is small.

In one exemplary embodiment of the disclosure, the image evaluation unit is configured such that the image data of the partial detection region are evaluable for a stamp in the objective protective glass, with the stamp forming a pattern.

A pattern can be introduced into the objective protective glass in the form of a stamp. A stamp cannot be easily removed.

In one exemplary embodiment of the disclosure, the image evaluation unit is configured such that the image data of the partial detection region are evaluable for a roughened surface on the objective protective glass.

A roughened surface at a detectable point on the objective protective glass has a lower transparency than a clear, transparent surface. The detection of an objective protective glass is possible if the objective protective glass has a roughened point that is captured by the partial detection region. A roughened point can already be introduced into the objective protective glass during the production if the shaping tool has the corresponding design. However, a roughened point can also be introduced into the objective protective glass after the shaping process, for example by grinding or etching. A roughened point can be applied on the upper side or on the underside of the objective protective glass.

In one exemplary embodiment of the disclosure, the image evaluation unit is configured such that the image data of the partial detection region are evaluable for a structured surface on the objective protective glass.

A structured surface at a point of the objective protective glass can have a lower transparency than a planar, non-structured surface. Owing to the structured surface, light changes can be brought about that are detectable in the partial detection region of the image sensor. A structured point can already be introduced into the objective protective glass during the production and be incorporated, for example, in the shaping tool. A structured point can be applied on the upper side or on the underside of the objective protective glass.

In one exemplary embodiment of the disclosure, the image evaluation unit is configured such that the image data of the partial detection region are evaluable for a contour of the protective glass module with the objective protective glass.

A detectable contour can be determined by the geometry of the protective glass module with the objective protective glass itself. The objective protective glass or another element of the protective glass module include visible edges and/or contours. One example is the peripheral contour of the plane-parallel plate of the protective glass module. In a two-piece protective glass module, the objective protective glass includes a region by which it is connected to the protective glass adapter, and it has visible edges and contours in said region. The protective glass module can be equipped with a grip region, at which it can be gripped by a user and be swapped without any need to touch the transparent optically relevant region. All these edges and regions form contours that are detectable by the partial detection region. The image evaluation unit can produce a signal when a contour of the protective glass module with the objective protective glass is detectable by the evaluation of the image data of the partial detection region of the image sensor.

In one exemplary embodiment of the disclosure, the image evaluation unit is configured such that the image data of the partial detection region are evaluable for a contour of the protective glass module which lies in a planar plane of the objective protective glass.

An objective protective glass can include a plane-parallel transparent plate, which forms in each case a planar plane on the upper side and on the underside of the transparent plate. In a protective glass module, a contour that is detectable by the partial detection region can be formed by a geometry or edge or bounding outline of the protective glass module which lies in one of these planar planes of the objective protective glass. This can be advantageous if the protective glass module is formed in two parts.

In one exemplary embodiment of the disclosure, the image evaluation unit is configured such that the image data of the partial detection region are evaluable for a contour of the protective glass module which does not lie in a planar plane of the objective protective glass.

An objective protective glass can include a plane-parallel transparent plate, which forms in each case a planar plane on the upper side and on the underside of the transparent plate. In a protective glass module, a contour that is detectable by the partial detection region can also be formed by a geometry or edge of the protective glass module which does not lie in one of these planar planes of the objective protective glass. This can be advantageous if the protective glass module is designed in one piece, or the protective glass module has contours above or below the plane-parallel plate.

In one exemplary embodiment of the disclosure, the image evaluation unit is configured such that the image data of the partial detection region are evaluable for an image on the objective protective glass.

An image is a two-dimensional graphic. An image can form a drawing with different lines and strokes and/or different color or tonal values. An image can also represent a pattern or a geometric shape. An image or an image detail can be captured by the partial detection region.

In one exemplary embodiment of the disclosure, the image evaluation unit is configured such that the image data of the partial detection region are evaluable for a mark arranged on the objective protective glass.

A mark forms an optical marking on the objective protective glass. A mark can have a specific color and/or depict a characteristic image that is distinctly evaluable by the image evaluation unit. A mark can also be applied retrospectively onto an existing objective protective glass. An existing stock of objective protective glasses can in this way be retrospectively provided with marks.

In one exemplary embodiment of the disclosure, the image evaluation unit is configured such that the image data of the partial detection region are evaluable for a mark arranged on the objective protective glass, wherein the mark is embodied as a spectral mark.

A spectral mark is a mark that has increased reflectivity in a specific wavelength range. The detection of this specific wavelength range on the image sensor simplifies the detection of the mark in the partial detection region. The detection can be limited to a delimited wavelength range, which can also lie outside the visible wavelength range. The visible wavelength range lies approximately between 380 nm and 780 nm.

In one exemplary embodiment of the disclosure, the image data of the mark are evaluable in a wavelength range of between 780 nm and 1500 nm.

The illumination light reflected at a mark on the objective protective glass can also be differentiated and evaluated in the captured image data of the partial detection region if it is analyzed in a specific wavelength range that is not assigned to the visible light. A wavelength range from a partial range of the near infrared that can be evaluated well is from 780 nm to 1500 nm. An image capture unit, for example a camera, can detect this wavelength range even if the observer cannot optically perceive it.

In one exemplary embodiment of the disclosure, the image capture unit includes at least two color channels, wherein an evaluation of the image data of the mark is limited to one color channel.

The image capture unit can include more than one image sensor. An image sensor can be assigned to one color channel. A partial detection region can also be assigned to an individual color channel. The detection of the mark can be limited to an individual color channel. One example of an image capture unit having more than one color channel is, for example, an RGB camera, which has one image sensor for each of the colors red, green, and blue. Alternatively, color cameras with other color filter sets are also possible, for example CYM, RWB, RYB, multi-junction pixels.

In one exemplary embodiment of the disclosure, the image capture unit includes at least two color channels, wherein an evaluation of the image data of the mark is limited to a color channel whose peak wavelength lies in the wavelength range between 400 nm and 500 nm or in the wavelength range between 500 nm and 600 nm or in the wavelength range between 600 nm and 700 nm.

The evaluation of the image data can be limited to a color channel whose peak wavelength is assigned to the blue color channel in a wavelength range between 400 nm and 500 nm. The evaluation can be limited to a color channel whose peak wavelength is assigned to the green color channel in a wavelength range between 500 nm and 600 nm. The evaluation can be limited to a color channel whose peak wavelength is assigned to the red color channel in a wavelength range between 600 nm and 700 nm. The spectral sensitive region of the respective color channel can also be larger than the specified wavelength range. The wavelength ranges of the color channels can al so overlap.

In one exemplary embodiment of the disclosure, the image capture unit includes at least two color channels, wherein an evaluation of the image data of the mark is limited to a color channel whose peak wavelength lies in the wavelength range between 400 nm and 500 nm.

The evaluation of the image data can be limited to a blue color channel. The spectral sensitive region can be larger than the specified region. The peak wavelength of the blue color channel lies between 400 nm and 500 nm.

In one exemplary embodiment of the disclosure, the image capture unit includes at least two color channels, wherein an evaluation of the image data of the mark is limited to a color channel whose peak wavelength lies in the wavelength range between 500 nm and 600 nm.

The evaluation of the image data can be limited to a green color channel. The spectral sensitive region can be larger than the specified region. The peak wavelength of the green color channel lies between 500 nm and 600 nm.

In one exemplary embodiment of the disclosure, the image capture unit includes at least two color channels, wherein an evaluation of the image data of the mark is limited to a color channel whose peak wavelength lies in the wavelength range between 600 nm and 700 nm.

The evaluation of the image data can be limited to a red color channel. The spectral sensitive region can be larger than the specified region. The peak wavelength of the red color channel lies between 600 nm and 700 nm.

In one exemplary embodiment of the disclosure, the image evaluation unit is configured such that the image data of the used detection region are correctable based on stored calibration data when an objective protective glass is detectable by evaluating the image data of the partial detection region.

The information relating to the optical effect of the objective protective glass in the detection beam path, for example an image offset or a distortion, can be stored in the form of previously ascertained calibration data in the image evaluation unit or in a memory of a further data processing system of the surgical microscope. Based on the calibration data, it is possible to calculate compensation of the optical effect of the objective protective glass in the detection beam path for the image data of the used detection region. Compensation of the optical effect can also be made available for further functions of the surgical microscope, for example for an autofocus function or for improving the presentation on a display apparatus.

BRIEF DESCRIPTION OF THE DRAWINGS

The disclosure will now be described with reference to the drawings wherein.

DESCRIPTION OF EXEMPLARY EMBODIMENTS

Figure 1:
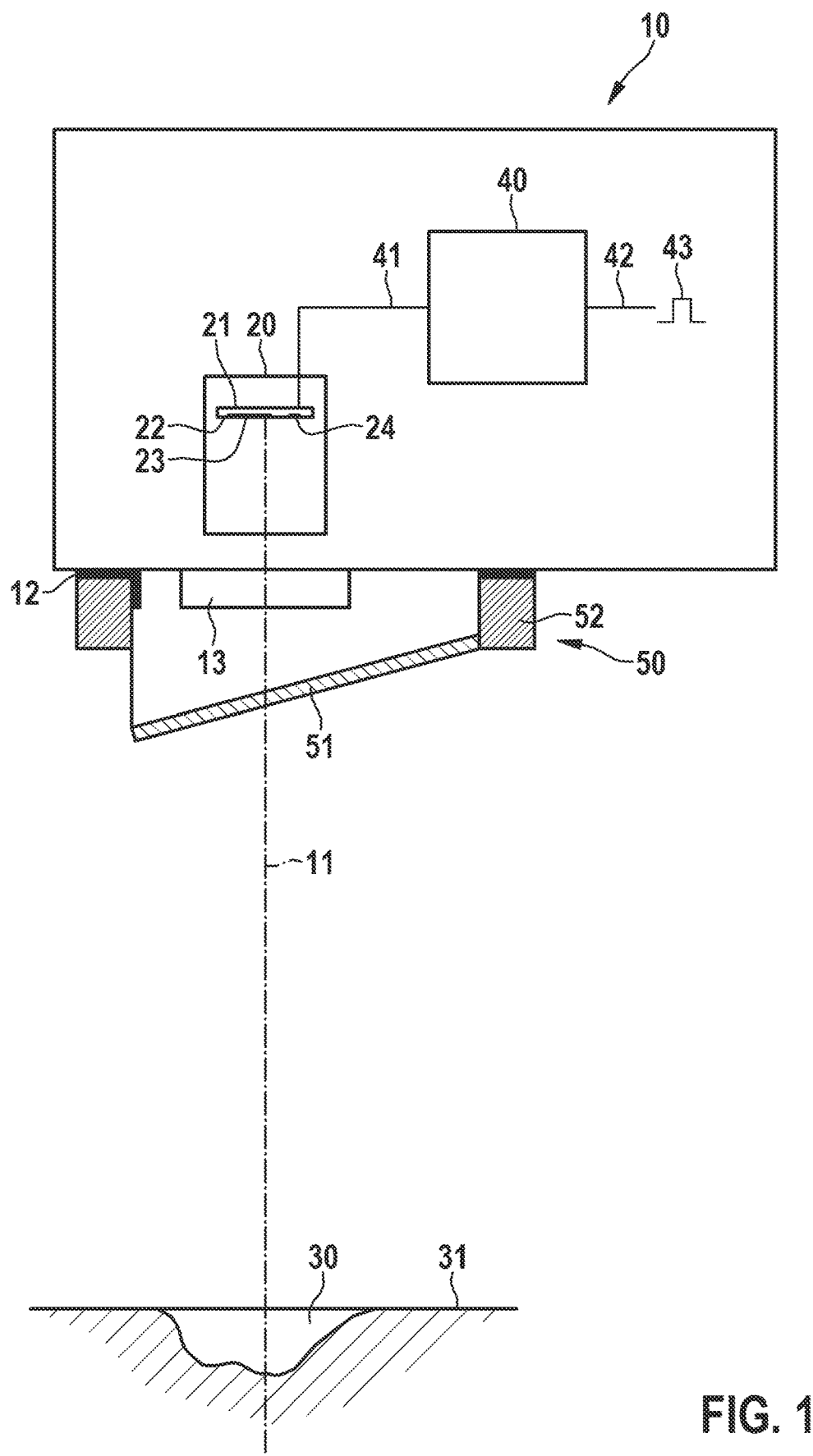
FIG. 1 shows a schematic illustration in a side view of a surgical microscope with a protective glass module according to a first exemplary embodiment of the disclosure.

FIG. 1 shows a schematic illustration in a side view of a first exemplary embodiment of a surgical microscope with a protective glass module.

A surgical microscope 10 includes an image capture unit 20 with an image sensor 21. A surgical site forms an object region 30 with an object plane 31. A detection beam path 11 is defined or guided from the object region 30 to the image sensor 21 of the image capture unit 20. The detection beam path 11 is illustrated schematically by the optical axis of the detection beam path 11. The optical axis of the detection beam path 11 is drawn as a dash-dotted line. Arranged in the detection beam path 11 is an objective 13, which causes the object region 30 with the object plane 31 to be imaged onto the image sensor 21. The objective 13 may be a camera optical unit. In one embodiment, the objective 13 is a main objective. The objective 13 can also enable imaging on the image sensor 21 in combination with an additional video objective (not illustrated). Further optics elements (not illustrated), for example a zoom system or an autofocus system, can be present between the objective 13 and the image sensor 21.

The surgical microscope 10 has, on its underside, a connection region 12 for attaching a protective glass module 50. The protective glass module 50 is attached with a form fit to the connection region 12. In this exemplary embodiment, the protective glass module 50 is embodied in two parts. The protective glass module 50 has a protective glass adapter 52 and an objective protective glass 51. The objective protective glass 51 includes an optically transparent plane-parallel plate, which is arranged with a defined inclination relative to the optical axis of the detection beam path 11. In this exemplary embodiment, the inclination angle of the objective protective glass 51 to a plane that is orthogonal to the optical axis of the detection beam path 11 is 15°. Owing to the form-fitting attachment of the protective glass adapter 52 to the connection region 12, the objective protective glass 51 is located at a defined distance and with a defined alignment with respect to the surgical microscope 10. The protective glass adapter 52 with the objective protective glass 51 forms a splash guard for the objective 13 and possible further optics components. The objective protective glass 51 forms a viewing opening for the image sensor 21 onto the object region 30.

A sterile protective sleeve (not illustrated), which is also referred to as a drape, can be attached to the periphery of the protective glass adapter 52. The sterile protective sleeve forms, together with the protective glass adapter 52 and the objective protective glass 51, a sterile barrier around the surgical microscope 10.

The image sensor 21 is connected to an image evaluation unit 40 via a data line 41. The image evaluation unit 40 is a data processing unit and can be formed by a computer, a signal processor, a microcontroller unit, or a graphics card, for example. The image evaluation unit 40 can include a software controller for computationally processing the image data. The image evaluation unit includes a memory or is connected to a memory. Calibration data can be stored in the memory. The image evaluation unit 40 has an output 42, which can output a signal 43. In an alternative exemplary embodiment, the calibration data can also be stored for the subsequent data processing at a different point away from the image evaluation unit 40.

The image sensor 21 has a detection region 22 which includes a large number of individual sensors. A part of the detection region 22 forms a used detection region 23. The object region 30 is imaged by the objective 13 onto the used detection region 23.

A number of individual sensors of the detection region 21 are defined as a partial detection region 24. The surface area of the detection region 22 taken up by the partial detection region 24 is significantly smaller than the surface area of the detection region 22 taken up by the used detection region 23.

Figure 5:
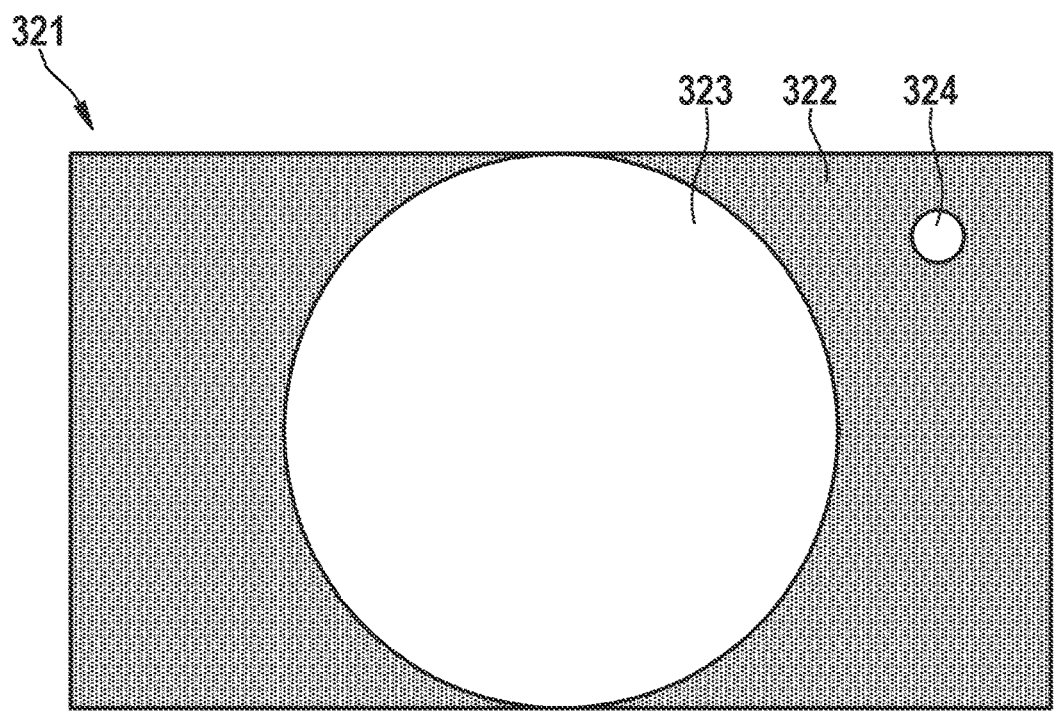
FIG. 5 shows a schematic illustration of a first exemplary embodiment of a detection region of an image sensor.
Figure 6:
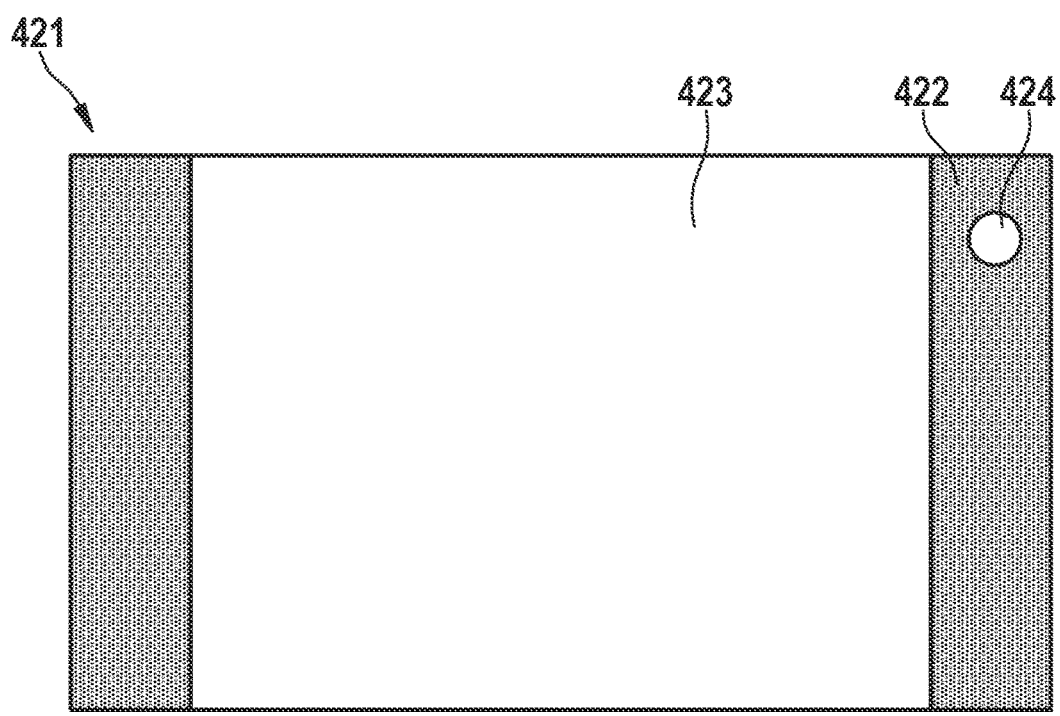
FIG. 6 shows a schematic illustration of a second exemplary embodiment of a detection region of an image sensor.

Two exemplary embodiments of an image sensor 21 with a used detection region 23 and a partial detection region 24 are illustrated in FIGS. 5 and 6.

When the protective glass module 50 with the objective protective glass 51 is attached to the surgical microscope 10 at the connection region 12, as illustrated in FIG. 1, the objective protective glass 51 has been inserted into the detection beam path 11. A detail or portion of the protective glass module 50 with the objective protective glass 51 is capturable by the partial detection region 24 of the image sensor 21.

The image evaluation unit 40, which is connected to the image sensor 21 via the data line 41, can read the image data, that is to say the sensor information from the used detection region 23 and the partial detection region 24, and computationally process them. If the evaluation of the image data of the partial detection region 24 leads to the result that an objective protective glass 51 is detectable, a signal 43 is output at the output 42 of the image evaluation unit 40. The system thus forms a detection apparatus for whether a protective glass module 50 with an objective protective glass 51 is attached to the connection region 12 of the surgical microscope 10.

The signal 43 can be output, for example, as a current signal, as a voltage signal or as a pulse signal. In an alternative exemplary embodiment, the signal 43 can be output by setting or resetting a memory area. The assignment of a software variable to a defined value is also possible.

The signal 43 can consequently control subsequent data processing for the image data of the image sensor 21. The signal 43 is output when the protective glass module 50 with the objective protective glass 51 is attached to the connection region 12 and the objective protective glass 51 has been inserted into the detection beam path 11. The signal 43 can control any further image processing that is integrated in the surgical microscope 10 or further peripheral data processing systems or display apparatuses.

The image data of the object region 30 detected by the used detection region 23 can have optical image errors due to the objective protective glass 51 that has been inserted in the detection beam path 11. These optical image errors in the image data can be computationally corrected. The assignment of position information for tracking functionalities can be corrected, and the measurement accuracy of the tracking functions can thus be improved. Any existing tracking accuracy without the objective protective glass 51 continues to be ensured even when an objective protective glass 51 is attached.

The information relating to the optical effect of the objective protective glass 51 in the detection beam path 11 can be stored in the form of previously determined calibration data in the data processing system of the surgical microscope 10, for example in a memory of the image evaluation unit 40. Based on the calibration data, it is possible to calculate compensation of the optical effect of the objective protective glass 51 in the detection beam path 11 for the image data of the used detection region 23. Optical image errors, for example distortion or image offset, are very quickly correctable using stored calibration data. Advantageously, this can be used for example for improving a real-time presentation on a display apparatus.

The image correction can be controlled automatically by the evaluation of the signal 43. The signal 43 can advantageously also control further functions of the surgical microscope 10, for example an autofocus function or the illumination brightness.

The signal 43 can be processed so as to be unnoticeable by the user, and so correction of the image data takes place automatically when the signal 43 for the detection of an objective protective glass 51 in the detection beam path 11 is output. However, in an alternative exemplary embodiment, this signal 43 can also additionally be output as user information on a screen. Outputting the signal as a visual signal, for example an LED display, or acoustic signal is also conceivable.

The signal 43 can also output visual and/or acoustic information to a user when the objective protective glass 51 has been removed but not reattached or interchanged. The surgical microscope 10 can thus be equipped with a notification function, which indicates the removal and non-reattachment of an objective protective glass 51.

Figure 9:
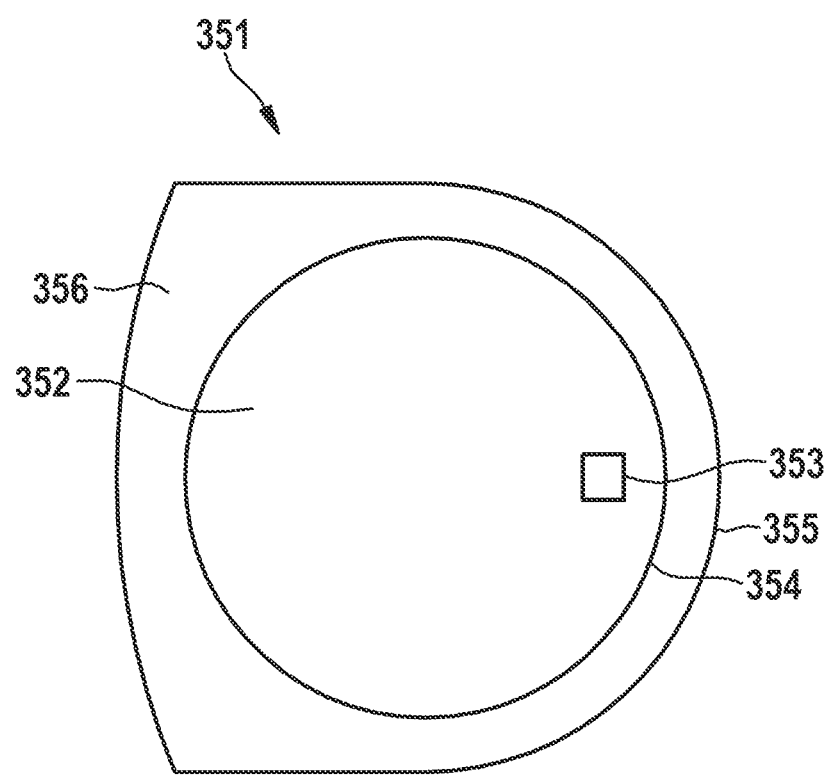
FIG. 9 shows a schematic illustration of an exemplary embodiment of an objective protective glass.

The image data of the partial detection region 24 can be evaluated on the basis of an optical feature or an optical property of the protective glass module 51. In one exemplary embodiment, the objective protective glass 51 can be detected by back-reflected illumination light. This exemplary embodiment is described in FIGS. 2 and 3. In one exemplary embodiment, the detection can take place on the basis of an optical element in or on the objective protective glass 51. An objective protective glass 51 with an optical element is shown in FIG. 9.

Figure 2:
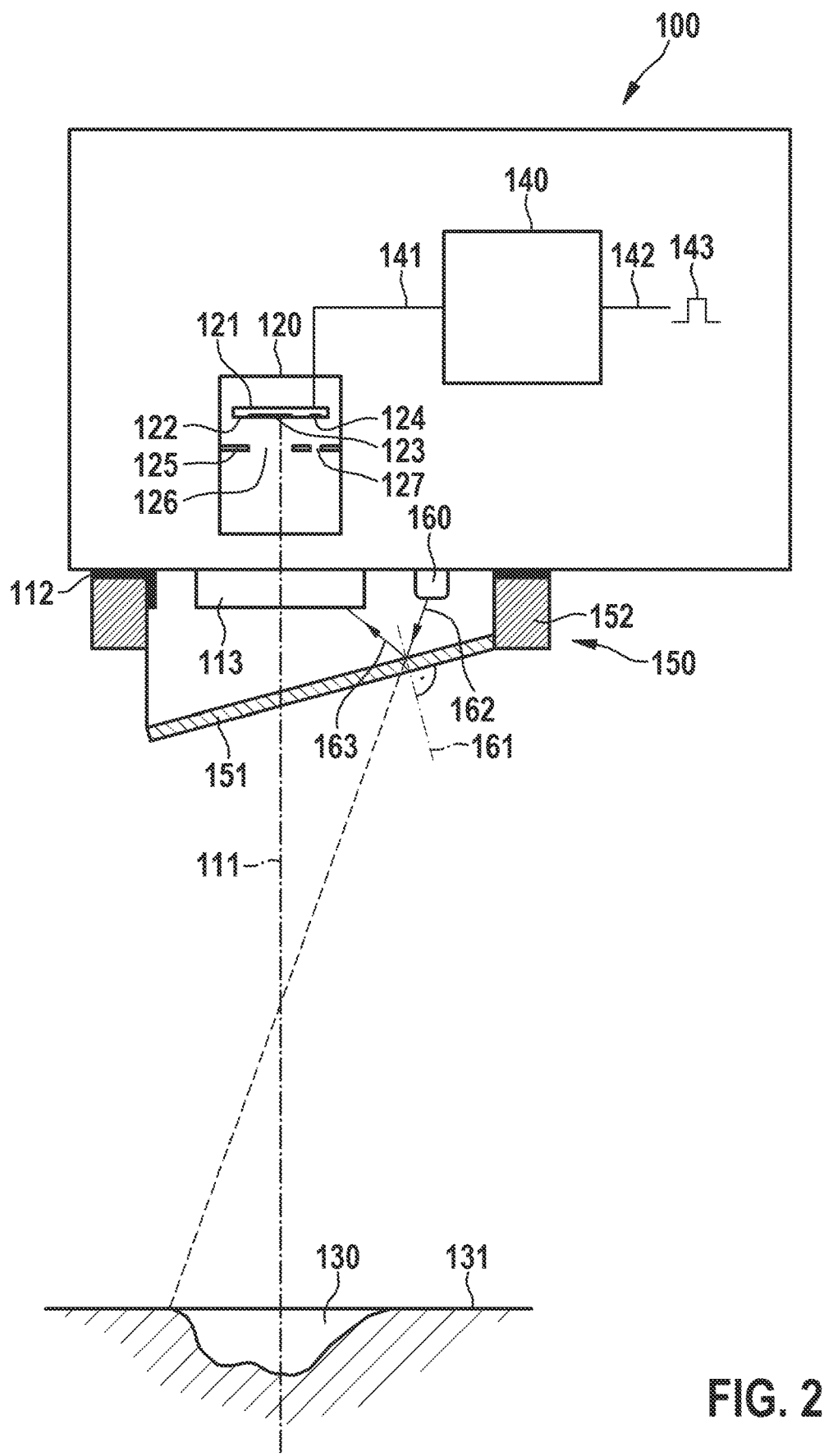
FIG. 2 shows a schematic illustration in a side view of a surgical microscope with a protective glass module and an illumination apparatus according to a second exemplary embodiment of the disclosure.

FIG. 2 shows a schematic illustration in a side view of a second exemplary embodiment of a surgical microscope with a protective glass module and an illumination apparatus.

A surgical microscope 100 includes the same components as the surgical microscope 10 in accordance with FIG. 1, with the reference signs being increased by 100. The surgical microscope 100 differs from the surgical microscope 10 in FIG. 1 in that an illumination apparatus 160 is arranged on the underside of the surgical microscope 100. In addition, a stop 125 is arranged upstream of an image sensor 121 in a detection beam path 111.

The detection beam path 111 is illustrated schematically by the optical axis of the detection beam path 111. The illumination apparatus 160 is arranged at a distance from the optical axis of the detection beam path 111 and forms a means of oblique illumination for an object region 130. The illumination apparatus 160 forms an illumination cone, which fully lights the object region 130. A marginal ray of the illumination cone, which is shown by way of example on the left, forms an illumination path 162. The illumination path 162 is shown as a dashed line. The illumination path 162 and the optical axis of the detection beam path intersect above the object plane 131.

Some of the illumination light emitted by the illumination apparatus 160 along the illumination path 162 is reflected at an objective protective glass 151 and guided to an objective 113 in a reflection path 163, which is illustrated by way of example. At the point at which the reflection at the objective protective glass 151 occurs, an orthogonal 161 to the objective protective glass 151 is shown as a dash-dotted line. The reflection path 163 is guided further to a partial detection region 124 of the image sensor 121.

The illustration in FIG. 2 is schematic. In reality, the working distance between the objective 113 and the object plane 113 is larger than shown in FIG. 2 and lies between 200 mm and 625 mm. The angle between the reflection path 163 and the optical axis of the detection beam path 111 is smaller than illustrated in FIG. 2.

The partial detection region 124 of the image sensor 121 is formed as it is shown in FIG. 5 or FIG. 6. The illumination light back-reflected by the objective protective glass 151, illustrated schematically by the reflection path 163, is detectable by the partial detection region 124 when the protective glass module 150 with the objective protective glass 151 is arranged at the connection region 112 of the surgical microscope 100.

If, on the other hand, the objective protective glass 151 has not been inserted into the detection beam path 111 or has been removed, no back-reflection of illumination light along the reflection path 163 onto the partial detection region 124 thus takes place. Consequently, no back reflection is detected in the partial detection region 124. An image evaluation unit 140, which is connected to the image sensor 121 via a data line 141, can evaluate the image data of the partial detection region 124. If an objective protective glass 151 is detected on the basis of the back-reflected illumination light onto the partial detection region 124, a signal 143 is produced at an output 142.

The stop 125 includes a first opening 126 and a second opening 127. The first opening 126 is assigned to the used detection region 123. The second opening 127 is assigned to the partial detection region 124. The stop 125 delimits the viewing region onto the image sensor 121 and has the effect of a field stop. The used detection region 123 and the partial detection region 124 are clearly delineated on the detection region 122 of the image sensor 121 by the stop 125. The second opening 127 forms a defined clearance for the back-reflected illumination light of the reflection path 163 onto the partial detection region 124.

The stop 125 advantageously reduces the radiation of reflection light that is incident on the image sensor 121. The stop 125 also delimits the used detection region 123, in which no reflections should occur. The positioning of the illumination apparatus 160, of an image recording apparatus 120 with the image sensor 121 and of the protective glass module 150 with the objective protective glass 151 are matched to one another in a manner such that the used detection region 123 is not affected by the back-reflection of the reflection path 163. The functionality of the used detection region 123 is thus not impaired by the illumination light that is reflected at the objective protective glass 151 and is guided along the reflection path 163 to the partial detection region 124.

The stop 125 additionally reduces the irradiance of the back-reflected illumination light onto the partial detection region 124 of the image sensor 121 to the required extent. In this way, the stop 125 has been advantageously inserted into the detection beam path 111 to reduce the power of the back-reflected light onto the image sensor. The back-reflection of the illumination light that has been emitted by the illumination apparatus 160 and reflected at the objective protective glass 151 could have a high radiant power which, without the stop 125, could affect the image sensor 121, for example by way of strong overexposure or a blooming effect. Arranging the stop 125 upstream of the image sensor 121 effectively reduces the radiant power of the back-reflected light onto the detection region 122 of the image sensor 121 and prevents overexposure or the blooming effect.

In one exemplary embodiment, a thin sensor protective plate (not illustrated) can be mounted upstream of the image sensor 121. In this exemplary embodiment, the stop 125 is arranged directly upstream of the sensor protective plate in the detection beam path 111. Due to the distance between the stop 125 and the image sensor 121 being slightly larger because of the sensor protective plate, the first opening 126 and the second opening 127 can also be configured to be slightly larger than the used detection region 123 or partial detection region 124 respectively assigned by way of said clearances. This ensures that the used detection region 123 and the partial detection region 124 on the image sensor 121 can be utilized fully all the way up to the respective peripheral region.

The stop 125 is optional. One embodiment variant (not illustrated) according to FIG. 2 can also be embodied without the stop 125.

In one exemplary embodiment, the detection can take place on the basis of an optical element in or on the objective protective glass 151. The optical element can be arranged for example at the point on the objective protective glass 151 at which the illumination light emitted by the illumination apparatus 160 along the illumination path 162 is reflected at the objective protective glass 151 at the point of the orthogonal 161 and guided in the reflection path 163 to the objective 113. This exemplary embodiment is advantageous if a back reflection is intended to be detected. However, the optical element in other exemplary embodiments can also be arranged at any other desired point on the objective protective glass 151. Arranging it at a different point than the reflection point mentioned above makes sense if reflections should be avoided on the image sensor 121 in principle. In a further exemplary embodiment, the objective protective glass 151 can also be arranged with a deviating positioning relative to the objective 113 in the detection beam path 111 in order to avoid reflections onto the image sensor 121 in principle but enable the detection of the optical element by way of the partial detection region 124. An exemplary embodiment of an objective protective glass 151 with an optical element is shown in FIG. 9. The optical element is detectable particularly well by way of the illumination light.

Figure 3:
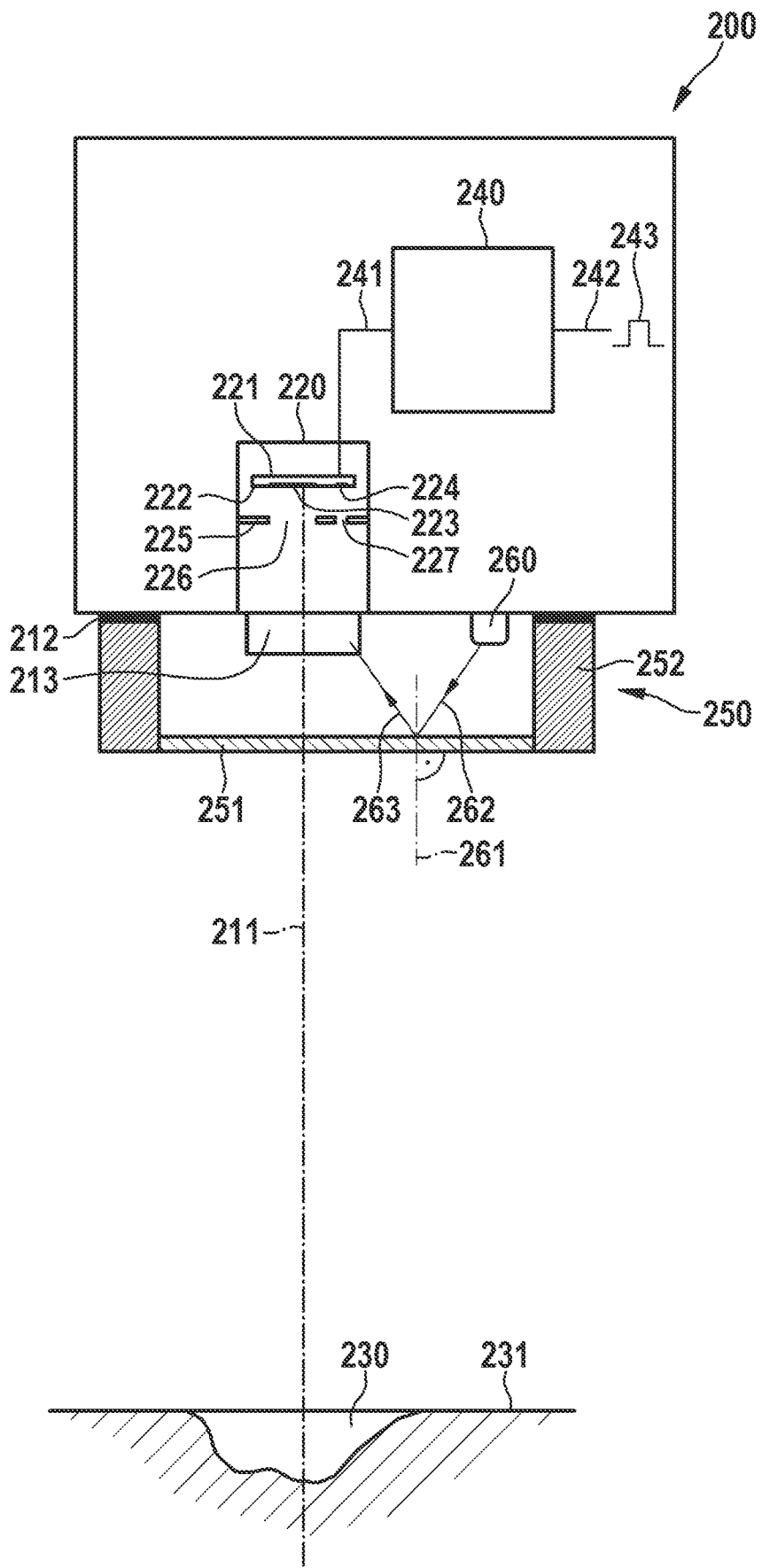
FIG. 3 shows a schematic illustration in a front view of a surgical microscope with a protective glass module and an illumination apparatus according to a third exemplary embodiment of the disclosure.

FIG. 3 shows a schematic illustration in a front view of a third exemplary embodiment of a surgical microscope with a protective glass module and an illumination apparatus.

Figure 4:
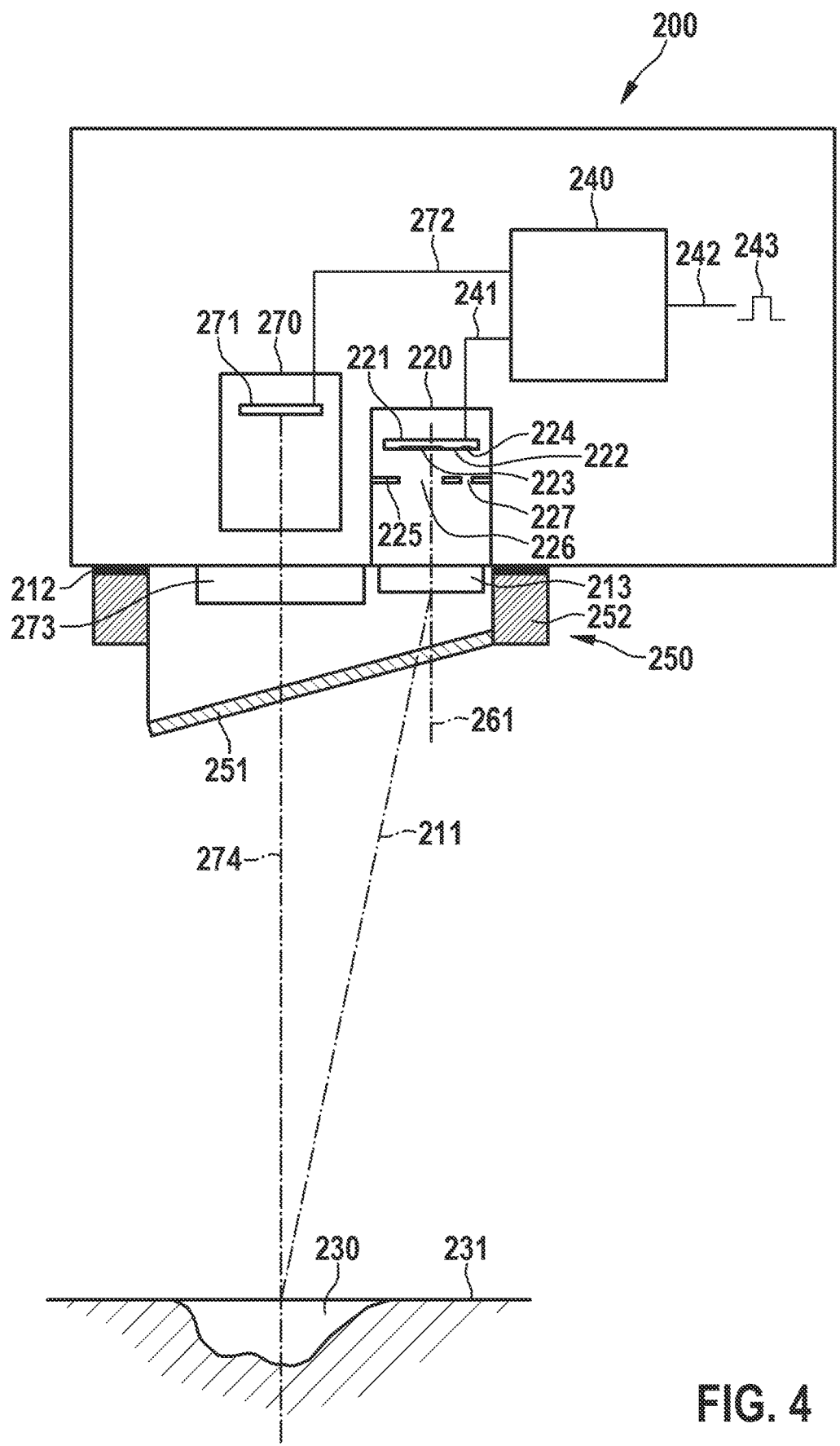
FIG. 4 shows a schematic illustration in a side view of the surgical microscope according to FIG. 3 according to the third exemplary embodiment of the disclosure.

FIG. 4 shows a schematic illustration in a side view of the third exemplary embodiment of the surgical microscope according to FIG. 3.

The surgical microscope 200 differs from the surgical microscope 10 according to FIG. 1 and from the surgical microscope 100 according to FIG. 2 in that it has two image recording units.

A first image recording unit forms an image capture unit 220, which is used for additional functions during the observation of an object region 230. A detection beam path 211 is guided through an objective 213 from the object region 230 to an image sensor 221 of the image capture unit 220. The detection beam path 211 is illustrated schematically by the optical axis of the detection beam path 211. The optical axis of the detection beam path 211 is drawn as a dash-dotted line. The image capture unit 220 has a detection region 222, wherein the majority of the sensor surface forms a used detection region 223 and a smaller part of the sensor surface forms a partial detection region 224.

The second image recording unit forms an observation unit 270, which is used to observe the object region 230. The observation unit 270 is illustrated only in FIG. 4, which shows the surgical microscope 200 in a side view. The observation unit 270 is not illustrated in FIG. 3, because it is arranged in a different plane.

The observation unit 270 can have a stereoscopic embodiment. An observation beam path 274 is guided from the object region 230 to an observation image sensor 271 of the observation unit 270. The observation beam path 274 is illustrated schematically by the optical axis of the observation beam path 274. The optical axis of the observation beam path 274 is drawn as a dash-dotted line. The observation beam path 274 is guided through a main objective 273. The image data of the observation unit 270 can be displayed on a display apparatus (not illustrated), for example a screen. The presentation on the display apparatus can take place in real time. The observation unit 270 and the image capture unit 220 can be formed by two separate cameras.

The surgical microscope 200 has, on its underside, a connection region 212 for attaching a protective glass module 250. The protective glass module 250 can be embodied in one piece or two pieces. In this exemplary embodiment, the protective glass module 250 is embodied in two parts. The protective glass module 250 has a protective glass adapter 252 and an objective protective glass 251. The protective glass module 250 substantially corresponds to the protective glass module 50, as is described in FIG. 1. However, the protective glass module 250 according to FIGS. 3 and 4 is dimensioned such that the main objective 273, an objective 213 which is assigned to the image capture unit 220, and the optical unit of an illumination apparatus 260 are protected against contamination.

The observation unit 270 and the image capture unit 220 are arranged in the surgical microscope 200 so as to be spatially separate from each other, as is illustrated in FIG. 4. The optical axis of the observation beam path 274 and the optical axis of the detection beam path 211 intersect in an object plane 231 in the object region 230. The optical axis of the observation beam path 274 and the optical axis of the detection beam path 211 consequently intersect the objective protective glass 251 in different regions. As a consequence, the image sensor 221 of the image capture unit 220 can capture a detail of the protective glass module 250 with the objective protective glass 251 that lies outside of the observation region of the observation image sensor 271 of the observation unit 270.

The partial detection region 224 is defined in a sensor region of the image sensor 221 that is assigned to said detail. The partial detection region 224 can thus capture a detail of the protective glass module 250 with the objective protective glass 251 that lies both outside of the used detection region 223 and also outside of the observation region of the observation image sensor 271.

The illumination device 260 is arranged on the underside of the surgical microscope 200. The illumination apparatus 260 is arranged at a distance from the optical axis of the detection beam path 211 and forms a means of oblique illumination for the object region 230. Some of the illumination light emitted by the illumination apparatus 260 is reflected at the objective protective glass 251. FIG. 3 schematically illustrates an illumination path 262, which is reflected at the objective protective glass 251 at the point of an orthogonal 261 and is guided in a reflection path 263 to the objective 213. The reflection path 263 is guided further to the partial detection region 224 of the image sensor 221.

The illustration in FIGS. 3 and 4 is schematic. The statements made for FIG. 2 with respect to the size and angle ratios shown and to the working distance also apply to FIGS. 3 and 4.

A stop 225 is arranged upstream of the image sensor 221. The stop 225 includes a first opening 226 that is assigned to the used detection region 223 and a second opening 227 that is assigned to the partial detection region 224. The stop 225 is arranged, as described for the exemplary embodiment according to FIG. 2, as a reflection protection upstream of the image sensor 221.

The stop 225 is optional. One embodiment variant (not illustrated) according to FIGS. 3 and 4 can also be embodied without the stop 225.

The image sensor 221 is connected to an image evaluation unit 240 via a data line 241. The image evaluation unit 240 can read the image data, that is to say the sensor information from the used detection region 223 and the partial detection region 224, and computationally process them. If the evaluation of the image data of the partial detection region 224 leads to the result that an objective protective glass 251 is detectable, a signal 243 is output at the output 242 of the image evaluation unit 240. The system thus forms a detection apparatus for whether a protective glass module 250 with an objective protective glass 251 is attached to the connection region 212 of the surgical microscope 200.

The observation image sensor 271 of the observation unit 270 is likewise connected to the image evaluation unit 240 via an image signal line 272. If the signal 243 that the objective protective glass 251 is attached to the connection region 212 of the surgical microscope 200 is generated in the image evaluation unit 240, this information can also be used to computationally correct the image data of the observation image sensor 271.

The used detection region 223 of the image capture unit 220 can be used for additional functions during the observation of an object region 230. An additional function can form a tracking function for tracking surgical instruments. Owing to the detection of the objective protective glass 251 in the detection beam path 211, optical image errors in the image data of the used detection region 223 can be computationally corrected. The assignment of position information for the tracking functionalities can be corrected, and the measurement accuracy of the tracking functions can thus be improved.

The detail of the object region 230 imaged on the used detection region 223 can be smaller than the detail of the object region 230 that is imaged on the observation image sensor 271. The used detection region 223 can be limited to a partial region of the object region 230 if the additional function is not applied to the entire visual region of the object region 230.

In one exemplary embodiment, the object region 230 capturable by the used detection region 223 can also be larger than the detail of the object region 230 that is imaged on the observation image sensor 271. In this way, surgical instruments that project into the peripheral region of the object region are also capturable. For example, it is thus also possible to reliably detect instruments that project only by way of the instrument tip into the object region 230 observable through the used detection region 223.

In one exemplary embodiment, the detection can take place on the basis of an optical element in or on the objective protective glass 251. The optical element can be arranged here for example at the point on the objective protective glass 251 at which the illumination light emitted by the illumination apparatus 260 along the illumination path 262 is reflected at the objective protective glass 251 at the point of the orthogonal 261 to the objective protective glass 251 and guided in the reflection path 263 to the objective 213. This exemplary embodiment is advantageous if a back reflection is intended to be detected. However, the optical element in an exemplary embodiment can also be arranged at another point on the objective protective glass 251. Arranging it at a different point than the reflection point mentioned above makes sense if reflections should be avoided on the image sensor 221 in principle. In a further exemplary embodiment, the objective protective glass 251 can also be arranged with a deviating positioning relative to the objective 213 in the detection beam path 211 in order to avoid reflections onto the image sensor 221 in principle but enable the detection of the optical element by way of the partial detection region 224. An exemplary embodiment of an objective protective glass 251 with an optical element is shown in FIG. 9.

FIG. 5 shows a schematic illustration of a first exemplary embodiment of a detection region of an image sensor.

A detection region 322 of an image sensor 321 includes a large number of individual sensors, which are arranged in rows and columns of a sensor matrix. A part of the detection region 322 forms a used detection region 323. In this exemplary embodiment, the used detection region 323 is round and lies at the center of the image sensor 321.

A number of individual sensors of the detection region 322 are defined as a partial detection region 324. The partial detection region 324 forms a region on the image sensor 321 that lies outside of the used detection region 323 and is therefore not assigned to the used detection region 323. Located between the partial detection region 324 and the used detection region 323 are individual sensors that are assigned neither to the used detection region 323 nor to the partial detection region 324. The partial detection region 324 is thus arranged at a distance from the used detection region 323. In this exemplary embodiment, the partial detection region 324 is round. The surface area of the detection region 322 taken up by the partial detection region 324 is significantly smaller than the surface area of the detection region 322 taken up by the used detection region 323.

In the exemplary embodiment according to FIG. 1, the image sensor 21 can be embodied like the image sensor 321 shown in FIG. 5. In an exemplary embodiment according to FIG. 2, the image sensor 121 can correspond to the image sensor 321 according to FIG. 5. In an exemplary embodiment according to FIGS. 3 and 4, the image sensor 221 can be embodied like the image sensor 321 shown in FIG. 5.

FIG. 6 shows a schematic illustration of a second exemplary embodiment of a detection region of an image sensor.

A detection region 422 of an image sensor 421 includes a large number of individual sensors, which are arranged in rows and columns of a matrix. A part of the detection region 422 forms a used detection region 423. In this exemplary embodiment, the used detection region 423 is rectangular and lies at the center of the image sensor 421.

A number of individual sensors of the detection region 422 form a partial detection region 424 that lies outside of the used detection region 423 and is therefore not assigned to the used detection region 423. In this exemplary embodiment, the partial detection region 424 is round. Located between the partial detection region 424 and the used detection region 423 are individual sensors that are assigned neither to the used detection region 423 nor to the partial detection region 424. The partial detection region 424 is thus arranged at a distance from the used detection region 423. The partial detection region 424 encompasses a significantly smaller surface area on the image sensor 421 than the used detection region 323.

In the exemplary embodiment according to FIG. 1, the image sensor 21 can be embodied like the image sensor 421 shown in FIG. 6. In an exemplary embodiment according to FIG. 2, the image sensor 121 can correspond to the image sensor 421 according to FIG. 6. In an exemplary embodiment according to FIGS. 3 and 4, the image sensor 221 can be embodied like the image sensor 421 shown in FIG. 6.

In an alternative exemplary embodiment (not illustrated), the partial detection region 324 according to FIG. 5 or the partial detection region 424 according to FIG. 6 can also be defined to be rectangular or square.

Figure 7:
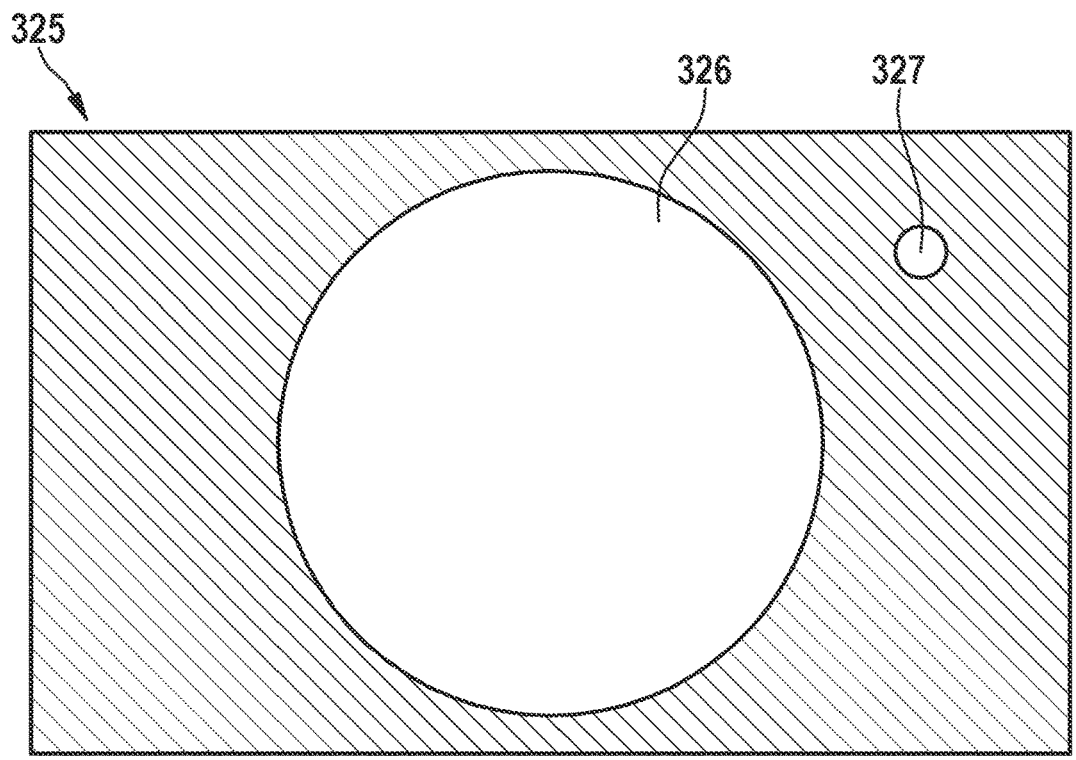
FIG. 7 shows a schematic illustration of a first exemplary embodiment of a stop.

FIG. 7 shows a schematic illustration of a first exemplary embodiment of a stop.

A rectangular stop 325 includes a first opening 326 and a second opening 327. The first opening 326 and the second opening 327 are each round. The first opening 326 is arranged at the center of the stop 325 and is significantly larger than the second opening 327, which is located at the peripheral region of the stop 325.

The stop 325 according to FIG. 7 is embodied to be arranged upstream of an image sensor 321 according to FIG. 5. The first opening 326 is assigned to the used detection region 323 and the second opening 327 is assigned to the partial detection region 324.

Figure 8:
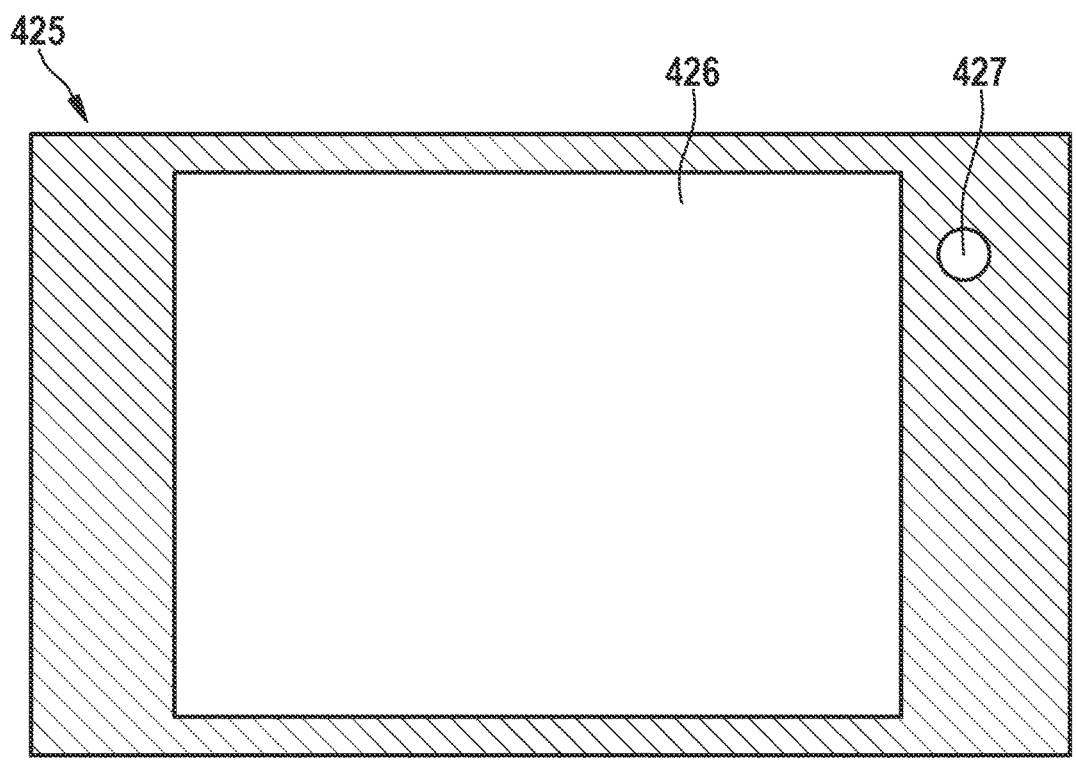
FIG. 8 shows a schematic illustration of a second exemplary embodiment of a stop.

FIG. 8 shows a schematic illustration of a second exemplary embodiment of a stop.

A rectangular stop 425 includes a first opening 426 and a second opening 427. The first opening 426 is rectangular. The second opening 427 is round. The first opening 426 is arranged at the center of the stop 425 and is significantly larger than the second opening 427, which is located at the peripheral region of the stop 425.

The stop 425 according to FIG. 8 is embodied to be arranged upstream of an image sensor 421 according to FIG. 6. The first opening 426 is assigned to the used detection region 423 and the second opening 427 is assigned to the partial detection region 424.

FIG. 9 shows a schematic illustration of an exemplary embodiment of an objective protective glass.

An objective protective glass 351, which is schematically illustrated, can either form a single-piece protective glass module or be a separate component part of a two-piece protective glass module. The objective protective glass 351 includes a transparent surface 352 and a peripheral region 356. The peripheral region 356 forms a grip region so that the objective protective glass 351 can be gripped by a user without touching the transparent surface 352. The peripheral region 356 also includes a connection region. In the case of a one-piece protective glass module, said connection region formed by the peripheral region 356 is compatible with the connection region of the surgical microscope. In the case of a two-piece protective glass module, the connection region formed by the peripheral region 356 can be attached to a protective glass adapter. In one exemplary embodiment, the peripheral region 356 can be slid into a guide of the protective glass adapter.

The objective protective glass 351 includes an optical element 353. The optical element 353 changes the optical property of the objective protective glass 351 at this point. The optical element 353 can bring about a change in the reflection property, the refractive index, the transparency or an intensity change or brightness change at this point.

In one exemplary embodiment, the optical element 353 can be formed by a stamp. The stamp is a three-dimensional contour including elevations and/or depressions. In one exemplary embodiment, the optical element 353 can include a two-dimensional image. In one exemplary embodiment, the optical element 353 can be formed by a logo. The logo can be embodied as a two-dimensional image or as a three-dimensional stamp. An image or a stamp can also have a defined geometric shape, for example depict a circle, a square, a triangle or a letter or a number. In one exemplary embodiment, the optical element 353 can be a pattern. In one exemplary embodiment, the optical element 353 can be a structured surface. In one exemplary embodiment, the optical element 353 can be a hologram. In one exemplary embodiment, the optical element 353 can include optical lens elements. In one exemplary embodiment, the optical element 353 can be a diffractive optical element. In one exemplary embodiment, the optical element 353 can have a grating.

In one exemplary embodiment, the optical element 351 can be formed by a mark. In one exemplary embodiment, the mark is embodied as a spectral mark, that is to say the mark is detectable particularly well by an image sensor in a specific wavelength range, for example in a wavelength range between 780 nm and 1500 nm.

For the exemplary embodiments stated above, the partial detection region of the image sensor is configured to capture the optical element 353 of the objective protective glass 351. The image evaluation unit can evaluate the image data of the partial detection region and check whether the optical element 353 of the objective protective glass is present in the image data and is thus evaluable. It is thus detectable whether the objective protective glass 351 is arranged at the surgical microscope.

The optical element 353 is arranged at the periphery of the transparent surface 352. Consequently, the optical element 353 lies outside of the detection region of the surgical microscope. The optical element lies outside of the used detection region that is capturable by the image sensor and is capturable only by the partial detection region.

The objective protective glass 351 has a first contour 354 between the peripheral region 356 and the transparent surface 352. The first contour 354 has a constructive form and is visible because the transparent surface 352 is arranged at an inclination angle of 15° relative to a plane that the peripheral region 356 defines.

In one exemplary embodiment of the surgical microscope, the partial detection region of the image sensor is embodied to capture a contour of the objective protective glass 351. The image evaluation unit can evaluate the image data of the partial detection region and check whether a contour of the objective protective glass 351 is evaluable in the image data. A detectable contour is consequently given by the geometry of the objective protective glass 351. One example of a detectable contour is the first contour 354. A further example of a detectable contour is a second contour 355, which is formed by the outer edge of the peripheral region 356.

In one exemplary embodiment, the objective protective glass 351 can also be formed without a peripheral region 356. One example of this is an exemplary embodiment (not illustrated) of the objective protective glass 351 as a plane-parallel plate which has been inserted as a protective glass adapter in a silicone ring and thus forms a protective glass module. A detectable contour can be formed for example by the outer periphery of the plane-parallel plate or an edge of the silicone ring.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS 10, 100, 200 Surgical microscope
11, 111, 211 Detection beam path, optical axis
12, 112, 212 Connection region for a protective glass module
13, 113, 213 Objective
20, 120, 220 Image capture unit
21, 121, 221, 321, 421 Image sensor
22, 122, 222, 322, 422 Detection region
23, 123, 223, 323, 423 Used detection region
24, 124, 224, 324, 424 Partial detection region
30, 130, 230 Object region
31, 131, 231 Object plane
40, 140, 240 Image evaluation unit
41, 141, 241 Data line
42, 142, 242 Output
43, 143, 243 Signal
50, 150, 250 Protective glass module
51, 151, 251, 351 Objective protective glass
52, 152, 252 Protective glass adapter
125, 225, 325, 425 Stop
126, 226, 326, 426 First opening
127, 227, 327, 427 Second opening
160, 260 Illumination apparatus
161, 261 Orthogonal
162, 262 Illumination path
163, 263 Reflection path
270 Observation unit
271 Observation image sensor
272 Image signal line
273 Main objective
274 Observation beam path, optical axis
352 Transparent surface
353 Optical element
354 First contour
355 Second contour
356 Peripheral region

What is claimed is:

1. A surgical microscope, comprising:
an image capture unit having an image sensor;
a detection beam path defined from an object region to the image sensor of the image capture unit;
an image processor connected to the image sensor;
a connection region configured for attaching a protective glass module with an objective protective glass,
wherein the connection region is configured such that, in an appropriate protective glass module which is attached to the connection region, the objective protective glass is inserted into the detection beam path,
wherein the image sensor has a detection region,
wherein the detection region has a used detection region for capturing the object region,
wherein the detection region has a partial detection region, which is not assigned to the used detection region,
wherein the image capture unit is configured such that a detail of the protective glass module with the objective protective glass is capturable by the partial detection region of the image sensor when the protective glass module with the objective protective glass is arranged at the connection region,
wherein the image processor is configured to generate a signal when the objective protective glass is detectable by an evaluation of image data of the partial detection region of the image sensor.

2. The surgical microscope as claimed in claim 1, further comprising:
an illumination apparatus configured to illuminate the object region with illumination light, wherein the illumination light reflected at the objective protective glass is detectable in the partial detection region of the image sensor when the protective glass module with the objective protective glass is arranged at the connection region.

3. The surgical microscope as claimed in claim 1, further comprising:
a stop arranged in the detection beam path upstream of the image sensor, wherein the stop has a first opening assigned to the used detection region, and a second opening assigned to the partial detection region.

4. The surgical microscope as claimed in claim 1, wherein the image processor is configured such that the image data of the partial detection region are evaluable for an optical element in or on the objective protective glass.

5. The surgical microscope as claimed in claim 1, wherein the image processor is configured such that the image data of the partial detection region are evaluable for a stamp in the objective protective glass.

6. The surgical microscope as claimed in claim 1, wherein the image processor is configured such that the image data of the partial detection region are evaluable for a logo on the objective protective glass.

7. The surgical microscope as claimed in claim 1, wherein the image processor is configured such that the image data of the partial detection region are evaluable for a pattern on the objective protective glass.

8. The surgical microscope as claimed in claim 1, wherein the image processor is configured such that the image data of the partial detection region are evaluable for a roughened surface on the objective protective glass.

9. The surgical microscope as claimed in claim 1, wherein the image processor is configured such that the image data of the partial detection region are evaluable for a structured surface on the objective protective glass.

10. The surgical microscope as claimed in claim 1, wherein the image processor is configured such that the image data of the partial detection region are evaluable for a contour of the protective glass module with the objective protective glass.

11. The surgical microscope as claimed in claim 1, wherein the image processor is configured such that the image data of the partial detection region are evaluable for an image on the objective protective glass.

12. The surgical microscope as claimed in claim 1, wherein the image processor is configured such that the image data of the partial detection region are evaluable for a mark arranged on the objective protective glass.

13. The surgical microscope as claimed in claim 12, wherein the image data of the mark are evaluable in a wavelength range of between 780 nm and 1500 nm.

14. The surgical microscope as claimed in claim 12, wherein the image capture unit comprises at least two color channels, and
wherein the evaluation of the image data of the mark is limited to a color channel whose peak wavelength lies in a wavelength range between 400 nm and 500 nm or in the wavelength range between 500 nm and 600 nm or in the wavelength range between 600 nm and 700 nm.

15. The surgical microscope as claimed in claim 1, wherein the image processor is configured such that the image data of the used detection region are correctable based on stored calibration data when an objective protective glass is detectable by evaluating the image data of the partial detection region.

16. The surgical microscope as claimed in claim 1, wherein the partial detection region is located at a predetermined location at a distance from the used detection region.

* * * * *